(12) United States Patent
Yan et al.

(10) Patent No.: US 9,119,858 B2
(45) Date of Patent: Sep. 1, 2015

(54) COMPOSITIONS AND METHODS FOR TREATING OR PREVENTING ANTHRACYCLINE INDUCED CARDIOTOXICITY

(71) Applicant: Genesys Research Institute, Brighton, MA (US)

(72) Inventors: Xinhua Yan, Boston, MA (US); James P. Morgan, Boston, MA (US); Lewis C. Cantley, Boston, MA (US)

(73) Assignee: Genesys Research Institute, Inc., Boston, MA (US)

( * ) Notice: Subject to any disclaimer, the term of this patent is extended or adjusted under 35 U.S.C. 154(b) by 0 days.

(21) Appl. No.: 13/971,281

(22) Filed: Aug. 20, 2013

(65) Prior Publication Data

US 2014/0057861 A1    Feb. 27, 2014

Related U.S. Application Data

(60) Provisional application No. 61/691,633, filed on Aug. 21, 2012.

(51) Int. Cl.
 *A61K 31/436* (2006.01)
 *A61K 31/517* (2006.01)
 *A61K 31/704* (2006.01)

(52) U.S. Cl.
 CPC ............. *A61K 31/517* (2013.01); *A61K 31/436* (2013.01); *A61K 31/704* (2013.01)

(58) Field of Classification Search
 CPC .. A61K 31/517; A61K 31/436; A61K 31/704
 See application file for complete search history.

(56) References Cited

U.S. PATENT DOCUMENTS

| | | | |
|---|---|---|---|
| 3,773,919 A | 11/1973 | Boswell et al. | |
| 3,832,253 A | 8/1974 | DiPalma et al. | |
| 3,854,480 A | 12/1974 | Zaffaroni | |
| 4,452,775 A | 6/1984 | Kent | |
| 4,485,045 A | 11/1984 | Regen | |
| 4,544,545 A | 10/1985 | Ryan et al. | |
| 4,667,014 A | 5/1987 | Nestor, Jr. et al. | |
| 4,748,034 A | 5/1988 | de Rham | |
| 5,075,109 A | 12/1991 | Tice et al. | |
| 5,239,660 A | 8/1993 | Ooi | |
| 2010/0183728 A1* | 7/2010 | Desai et al. ................... 424/489 |

FOREIGN PATENT DOCUMENTS

| | | |
|---|---|---|
| DE | 3218121 A1 | 11/1983 |
| EP | 36676 A1 | 9/1981 |
| EP | 52322 A2 | 5/1982 |
| EP | 0058481 A1 | 8/1982 |
| EP | 88046 A2 | 9/1983 |
| EP | 102324 A2 | 3/1984 |
| EP | 133988 A2 | 3/1985 |
| EP | 142641 A2 | 5/1985 |
| EP | 143949 A1 | 6/1985 |
| WO | WO-9524929 A2 | 9/1995 |

OTHER PUBLICATIONS

Wu et al, "PI3K Inhibitors for Cancer Therapy: What has been Achieved so Far", Current Medicinal Chemistry, 2009, vol. 16, pp. 916-930.*
Chickering, D., et al. "Poly(fumaric-co-sebacic) Microspheres as Oral Drug Delivery Systems", Biotechnology and Bioengineering, vol. 52, pp. 96-101. 1996.
Eppstein, D. et al., "Biological activity of liposome-encapsulated murine interferon γ is mediated by a cell membrane receptor", Proc. Natl. Acad. Sci. USA, vol. 82 pp. 3688-3692. Jun. 1985.
Fraley and Papahadjopoulos, "New generation liposomes: the engineering of an efficient vehicle for intracellular delivery of nucleic acids", TIBS, pp. 77-80. Mar. 1981.
Gregoriadis, "Liposomes for drugs and vaccines", Trends in Biotechnology, vol. 3, pp. 235-241. 1985.
Hwang et al., "Hepatic uptake and degradation of unilamellar sphingomyelin/cholesterol liposomes: A kinetic study", Proc. Natl. Acad. Sci. USA, vol. 77, pp. 4030-4034. Jul. 1980.
Langer, "Controlled release of macromolecules", Chemtech, pp. 98-105. Feb. 1982.
Langer et al., "Biocompatibility of polymeric delivery systems for macromolecules", Journal of Biomedical Materials Research, vol. 15, pp. 267-277. 1981.
Mathiowitz et al., "Biologically erodable microspheres as potential oral drug delivery systems", Nature, vol. 386, pp. 410-414. Mar. 1997.
Sidman et al., "Controlled Release of macromolecules and Pharmaceuticals from Synthetic Polypeptides Based on Glutamic Acid", Biopolymers, vol. 22, pp. 547-556. 1983.
Dai et al., "Lapatinib (Tykerb, GW572016) Reverses Multidrug Resistance in Cancer Cells by Inhibiting the Activity of ATP-Binding Cassette Subfamily B Member 1 and G member 2", Cancer Research, 2008, vol. 68, No. 19, pp. 7905-7914.
Siegel-Lakhai et al., "Phase I Pharmacokinetic Study of the Safety and Tolerability of Lapatinib (GW572016) in Combination with Oxaliplatin/Fluorouracil/Leucovorin (FOLFOX4) in Patients with Solid Tumors", Clinical Cancer Research, Aug. 1, 2007, vol. 13. No. 15, pp. 4495-4502.
Barry et al., "Anthracycline-induced cardiotoxicity: course, pathophysiology, prevention and management", Expert Opinion on Pharmacotherapy, 2007, vol. 8, No. 8, pp. 1039-1058.
Horenstein et al., "Molecular Basis of Anthracycline-Induced Cardiotoxicity and Its Prevention", Molecular Genetics and Metabolism, 2000, vol. 71, pp. 436-444.
Zambelli et al., "Predicting and preventing cardiotoxicity in the era of breast cancer targeted therapies. Novel molecular tools for clinical issues", The Breast, 2011, vol. 20, pp. 176-183.

* cited by examiner

*Primary Examiner* — Elli Peselev
(74) *Attorney, Agent, or Firm* — Mintz Levin Cohn Ferris Glovsky and Popeo, P.C.; David G. Conlin

(57) ABSTRACT

The invention features methods and compositions feature lapatinib and/or rapamycin for treating or preventing a cardiac condition induced by anthracycline treatment.

9 Claims, 4 Drawing Sheets

*, P<0.05 vs Control;
†, P<0.05 vs DOX

*, P<0.05 vs Control;
†, P<0.05 vs DOX

COMPOSITIONS AND METHODS FOR TREATING OR PREVENTING ANTHRACYCLINE INDUCED CARDIOTOXICITY

RELATED APPLICATIONS

This application claims the benefit of priority under 35 U.S.C. §119(e) to U.S. Provisional Application No. 61/691,633, filed Aug. 21, 2012, which is incorporated herein by reference in its entirety.

STATEMENT OF RIGHTS TO INVENTIONS MADE UNDER FEDERALLY SPONSORED RESEARCH

This work was supported by the following grants from the National Institutes of Health, Grant Nos: NHLBI (1R21HL106098-01A1). The government has certain rights in the invention.

BACKGROUND OF THE INVENTION

Anthracyclines are a class of antibiotics that are commonly used cancer chemotherapeutic agents. These are broad spectrum agents and they are used to treat a number of cancers including leukemias, lymphomas, breast cancer, uterine cancer, ovarian cancer, and lung cancer. Anthracyclines are effective cancer chemotherapeutics, however, their full potential usefulness is limited by an induced cardiotoxicity. The cardiotoxicity is related to a patient's cumulative lifetime dose of the agents, which is carefully monitored, with treatment being stopped upon reaching the maximum cumulative dose. Accordingly, the usefulness of anthracyclines would be extended if associated cardiotoxicity could be prevented or delayed. Moreover, despite these precautions, a number of patients experience cardiac damage following treatment with anthracyclines. Therefore, there is a need for compositions and methods of preventing or treating anthracycline induced cardiotoxicity.

SUMMARY OF THE INVENTION

As described below, the present invention provides compositions comprising lapatinib or rapamycin for treating or preventing cardiac toxicity associated with the use of chemotherapeutics (e.g., anthracyclines) and methods of using such compositions to treat or prevent cardiotoxicity.

In one aspect, the invention generally features a method of treating anthracycline induced cardiotoxicity involving administering an effective amount of lapatinib and/or rapamycin to a subject in need thereof, thereby treating the anthracycline induced cardiotoxicity.

In another aspect, the invention features a method of enhancing cardiac function or increasing survival in a subject treated with an anthracycline involving administering an effective amount of lapatinib to the subject, thereby improving cardiac function in the subject.

In another aspect, the invention features a method of treating or preventing cardiotoxicity induced by co-treatment with an anthracycline and a PI3K inhibitor involving administering an effective amount of lapatinib and/or rapamycin to a subject in need thereof, thereby treating or preventing the cardiotoxicity induced by co-treatment with doxorubicin and the PI3K inhibitor.

In yet another aspect, the invention features a method of treating or preventing cardiac hypertrophy induced by co-treatment with an anthracycline and a PI3K inhibitor involving administering an effective amount of lapatinib and/or rapamycin to a subject in need thereof, thereby treating or preventing the cardiac hypertrophy induced by co-treatment with doxorubicin and the PI3K inhibitor.

In another aspect, the invention features a kit for preventing or treating anthracycline induced cardiotoxicity comprising an effective amount of lapatinib and/or rapamycin and instructions for use.

In yet another aspect, the invention features a pharmaceutical composition comprising an effective amount of doxorubicin and an effective amount of lapatinib and/or rapamycin, and instructions for the administration of each.

In various embodiments of the above aspects, the methods reduce cardiac hypertrophy and adverse cardiac remodeling in the subject. In still other embodiments, the anthracycline is one or more of daunorubicin, doxorubicin, epirubicin, idarubicin, valrubicin, and mitoxantrone.

In one embodiment, the anthracycline is doxorubicin. In other embodiments of the above aspects, the PI3K inhibitor is any one or more of wortmannin, demethoxyviridin, LY294002, perifosine, CAL101, PX-866, BEZ235, SF1126, INK1117, IPI-145, GDC-0941, BKM120, XL147, XL765, Palomid 529, GSK1059615, ZSTK474, PWT33597, IC87114, TG100-115, CAL263, PI-103, GNE-477, CUDC-907, BYL719, GDC-0032, BGT226, GDC0980, PF4691502, PKI587, and AEZS-136. In one embodiment, the PI3K inhibitor is BEZ235. In one embodiment of the above aspects, the lapatinib is administered concurrently with the doxorubicin and PI3K inhibitor. In embodiments of the above aspects, the effective amount of lapatinib is from about 25 mg/kg to 100 mg/kg (e.g., 25, 30, 35, 40, 45, 50, 60, 75, 80, 90, 100 mg/kg) administered daily. In one embodiment, the effective amount of lapatinib is about 25 mg/kg administered daily. In other embodiments of the above aspects, the invention further involves determining the subject's cumulative lifetime dose of anthracycline and administering the effective amount of lapatinib and/or rapamycin if the cumulative lifetime dose is above a reference value. In still another embodiment of the above aspects, the subject is identified by echocardiography.

The invention provides compositions and methods for treating anthracycline induced cardiotoxicity. Compositions and articles defined by the invention were isolated or otherwise manufactured in connection with the examples provided below. Other features and advantages of the invention will be apparent from the detailed description, and from the claims.

DEFINITIONS

By "anthracycline" is meant a class of drugs that are commonly used as a chemotherapeutic agent. Representative examples of anthracyclines include: daunorubicin, doxorubicin (also termed adriamycin), epirubicin, idarubicin, valrubicin, and mitoxantrone.

By "lapatinib" or "N-[3-chloro-4-[(3-fluorophenyl)methoxy]phenyl]-6-[5-[(2-methylsulfonylethylamino)methyl]-2-furyl]quinazolin-4-amine" is meant a dual tyrosine kinase inhibitor that is used for the treatment of various solid tumors including breast cancer. Lapatinib has the following structure:

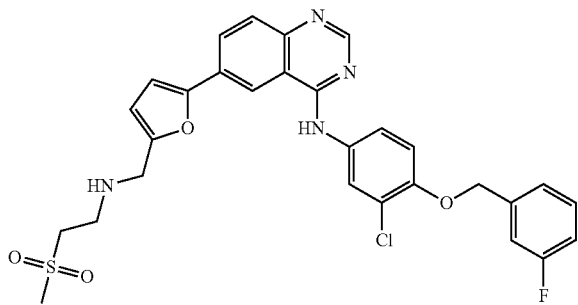 [SMILES: CS(=O)(=O)CCNCc1ccc(-c2ccc3ncnc(Nc4ccc(OCc5cccc(F)c5)c(Cl)c4)c3c2)o1]

By "BEZ235" or "2-methyl-2(4-[3-methyl-2-oxo-8-(quinolin-3-yl)-2,3-dihydro-1H-imidazo[4,5-c]quinolin-1-yl]phenyl)propanenitrile is meant a PI3K inhibitor having the following structure:

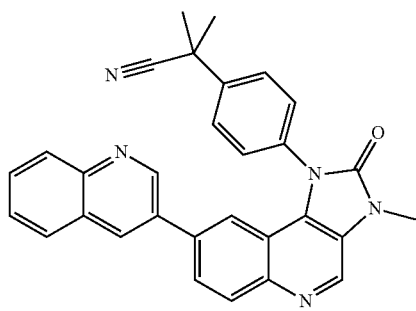 [SMILES: Cn1c(=O)n(-c2ccc(C(C)(C)C#N)cc2)c2c3cc(-c4cnc5ccccc5c4)ccc3ncc21]

By "PI3K inhibitor" is meant an agent that inhibits the activity of phosphoinositide 3-kinase. Non-limiting examples of PI3K inhibitors include wortmannin, demethoxyviridin, LY294002, perifosine, CAL101, PX-866, BEZ235, SF1126, INK1117, IPI-145, GDC-0941, BKM120, XL147, XL765, Palomid 529, GSK1059615, ZSTK474, PWT33597, IC87114, TG100-115, CAL263, PI-103, GNE-477, CUDC-907, and AEZS-136.

By "cardiac hypertrophy" is meant any undesirable cardiac muscle growth, increase in cardiac chamber mass relative to body size, or increase in cardiac chamber wall thickness at normal or increased chamber volume.

By "enhancing cardiac function" is meant producing a beneficial alteration in the pumping performance and capacity of the heart. In one embodiment, the method increases cardiac function by at least about 10%, 25%, 50%, 75% or more. Methods for measuring cardiac function are known in the art and described herein.

By "echocardiography" or "cardiac ultrasound" is meant a sonogram of the heart used to generate an accurate assessment of the velocity of blood at any point during the cardiac cycle.

By "end-systolic volume (ESV)" is meant the volume of blood in a ventricle at the end of contraction and represents the smallest volume of blood in the ventricle at any point in the cardiac cycle.

By "end-diastolic volume (EDV)" is meant the volume of blood in a ventricle at the end load or filing in.

By "increasing survival" is meant an increase in the amount of time a treated subject lives relative to an untreated corresponding control subject. For example, an increase in survival of at least about 2, 3, 4, or 5 weeks. Preferably, survival is increased by at least about 1, 2, 3, 4, 5, 6, 7, 8, 9, 10, 11, or 12 months. In other embodiments, survival is increased by at least 1, 2, 3, 4, or 5 years.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in a clinical parameter or biomarker (e.g., polypeptide, polynucleotide level) as detected by standard art known methods such as those described herein. As used herein, an alteration includes a 10%, 25%, 40%, 50% or greater change.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "modulation" is meant any alteration (e.g., increase or decrease) in a biological function or activity.

As used herein, "obtaining" as in "obtaining an agent" includes synthesizing, purchasing, or otherwise acquiring the agent.

By "increases" or reduces" is meant a positive or negative alteration, respectively, of at least about 10%, 25%, 50%, 75%, or 100%.

By "reference" is meant a standard or control condition.

By "specifically binds" is meant a compound or antibody that recognizes and binds a polypeptide of the invention, but which does not substantially recognize and bind other molecules in a sample, for example, a biological sample, which naturally includes a polypeptide of the invention.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," "treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

Figure 1:
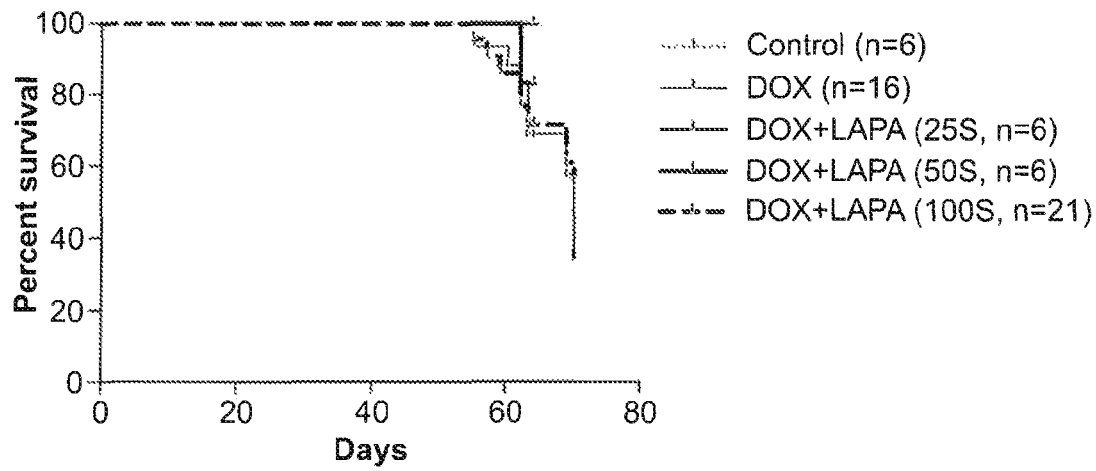
FIG. 1 is a line graph showing the survival curve of mice treated with doxorubicin followed by treatment with various doses of lapatinib.

The invention features compositions comprising lapatinib or rapamycin that are useful for treating anthracycline induced cardiotoxicity, as well as preventing anthracycline and PI3-mTOR kinase inhibitor BEZ235 induced cardiotoxicity. The invention is based, at least in part, on the discovery that lapatinib and rapamycin increased the survival and cardiac function of mice treated with doxorubicin, or doxorubicin and BEZ235.

The methods herein include administering to the subject (including a subject identified as in need of such treatment) an effective amount of a compound described herein, or a composition described herein to produce a beneficial effect on a cardiac tissue. Identifying a subject in need of such treatment can be in the judgment of a subject or a health care professional and can be subjective (e.g. opinion) or objective (e.g. measurable by a test or diagnostic method).

As reported in more detail below, each of lapatinib and rapamycin was found to treat cardiotoxicity induced by anthracyclines. Anthracyclines are commonly used chemotherapeutics for the treatment of many cancers. The major limiting side effect of anthracycline use is the induction of cardiotoxicity. For this reason, a patients cumulative anthracycline dosing is closely monitored as is cardiac function. Once a patient has received anthracycline doses surpassing a threshold amount or upon a finding of impaired cardiac function, the anthracycline treatment is stopped. Lapatinib is dual tyrosine kinase inhibitor that is approved for use in treating HER2 positive breast cancer. As shown herein, Lapatinib treatment increased the survival of animals that had been treated with the anthracycline doxorubicin. In addition, Lapatinib treatment was shown to improve cardiac function in animals treated with doxorubicin. In addition, co-treatment with doxorubicin and the PI3K inhibitor, BEZ235, was found to result in cardiotoxicity. Lapatinib treatment was shown to prevent the cardiotoxicity of co-treatment with doxorubicin and BEZ235.

The present invention provides methods of treating or preventing disease and/or disorders or symptoms thereof which comprise administering a therapeutically effective amount of a pharmaceutical composition comprising a compound of the formulae herein to a subject (e.g., a mammal such as a human). Thus, one embodiment is a method of treating or preventing a subject suffering from or susceptible to anthracycline or PI3K-mTOR inhibitor BEZ235 induced cardiotoxicity. The method includes the step of administering to the mammal a therapeutic amount lapatinib sufficient to treat the disease or disorder or symptom thereof, under conditions such that the disease or disorder is treated.

Any number of standard methods are available for assaying cardiovascular function. Preferably, cardiovascular function in a subject (e.g., a human) is assessed using non-invasive means, such as measuring net cardiac ejection (ejection fraction, fractional shortening, and ventricular end-systolic volume) by an imaging method such echocardiography, nuclear or radiocontrast ventriculography, or magnetic resonance imaging, and systolic tissue velocity as measured by tissue Doppler imaging. Systolic contractility can also be measured non-invasively using blood pressure measurements combined with assessment of heart outflow (to assess power), or with volumes (to assess peak muscle stiffening). Measures of cardiovascular diastolic function include ventricular compliance, which is typically measured by the simultaneous measurement of pressure and volume, early diastolic left ventricular filling rate and relaxation rate (can be assessed from echoDoppler measurements). Other measures of cardiac function include myocardial contractility, resting stroke volume, resting heart rate, resting cardiac index (cardiac output per unit of time [L/minute], measured while seated and divided by body surface area [$m^2$])) total aerobic capacity, cardiovascular performance during exercise, peak exercise capacity, peak oxygen ($O_2$) consumption, or by any other method known in the art or described herein. Measures of vascular function include determination of total ventricular afterload, which depends on a number of factors, including peripheral vascular resistance, aortic impedance, arterial compliance, wave reflections, and aortic pulse wave velocity.

Methods for assaying cardiovascular function include any one or more of the following: Doppler echocardiography, 2-dimensional echo-Doppler imaging, pulse-wave Doppler, continuous wave Doppler, oscillometric arm cuff, tissue Doppler imaging, cardiac catheterization, magnetic resonance imaging, positron emission tomography, chest X-ray, X-ray contrast ventriculography, nuclear imaging ventriculography, computed tomography imaging, rapid spiral computerized tomographic imaging, 3-D echocardiography, invasive cardiac pressures, invasive cardiac flows, invasive cardiac pressure-volume loops (conductance catheter), non-invasive cardiac pressure-volume loops.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

Pharmaceutical Compositions

The present invention features pharmaceutical preparations comprising lapatinib together with pharmaceutically acceptable carriers, where the compounds provide for the treatment of virtually any cardiac indication induced by anthracycline treatment or co-treatment of an anthracycline with a PI3K inhibitor. Pharmaceutical preparations of the invention have both therapeutic and prophylactic applications. In one embodiment, a pharmaceutical composition includes an effective amount of lapatinib. The compositions should be sterile and contain a therapeutically effective amount of lapatinib in a unit of weight or volume suitable for administration to a subject (e.g., a human patient). The compositions and combinations of the invention can be part of a pharmaceutical pack, where the lapatinib is present in individual dosage amounts.

Pharmaceutical compositions of the invention to be used for prophylactic or therapeutic administration should be sterile. Sterility is readily accomplished by filtration through sterile filtration membranes (e.g., 0.2 µm membranes), by gamma irradiation, or any other suitable means known to those skilled in the art. Therapeutic compositions generally are placed into a container having a sterile access port, for example, an intravenous solution bag or vial having a stopper pierceable by a hypodermic injection needle. These compositions ordinarily will be stored in unit or multi-dose containers, for example, sealed ampoules or vials, as an aqueous solution or as a lyophilized formulation for reconstitution.

Lapatinib or rapamycin may be combined, optionally, with a pharmaceutically acceptable excipient. The term "pharmaceutically-acceptable excipient" as used herein means one or more compatible solid or liquid filler, diluents or encapsulating substances that are suitable for administration into a human. The term "carrier" denotes an organic or inorganic ingredient, natural or synthetic, with which the active ingredient is combined to facilitate administration. The components of the pharmaceutical compositions also are capable of being co-mingled with lapatinib and/or rapamycin, and with each other, in a manner such that there is no interaction that would substantially impair the desired pharmaceutical efficacy.

Compounds of the present invention can be contained in a pharmaceutically acceptable excipient. The excipient preferably contains minor amounts of additives such as substances that enhance isotonicity and chemical stability. Such materials are non-toxic to recipients at the dosages and concentrations employed, and include buffers such as phosphate, citrate, succinate, acetate, lactate, tartrate, and other organic acids or their salts; tris-hydroxymethylaminomethane (TRIS), bicarbonate, carbonate, and other organic bases and their salts; antioxidants, such as ascorbic acid; low molecular weight (for example, less than about ten residues) polypeptides, e.g., polyarginine, polylysine, polyglutamate and polyaspartate; proteins, such as serum albumin, gelatin, or immunoglobulins; hydrophilic polymers, such as polyvinylpyrrolidone (PVP), polypropylene glycols (PPGs), and polyethylene glycols (PEGs); amino acids, such as glycine, glutamic acid, aspartic acid, histidine, lysine, or arginine; monosaccharides, disaccharides, and other carbohydrates including cellulose or its derivatives, glucose, mannose, sucrose, dextrins or sulfated carbohydrate derivatives, such as heparin, chondroitin sulfate or dextran sulfate; polyvalent metal ions, such as divalent metal ions including calcium ions, magnesium ions and manganese ions; chelating agents, such as ethylenediamine tetraacetic acid (EDTA); sugar alcohols, such as mannitol or sorbitol; counterions, such as sodium or ammonium; and/or nonionic surfactants, such as polysorbates or poloxamers. Other additives may be included, such as stabilizers, anti-microbials, inert gases, fluid and nutrient replenishers (i.e., Ringer's dextrose), electrolyte replenishers, and the like, which can be present in conventional amounts.

The compositions, as described above, can be administered in effective amounts. The effective amount will depend upon the mode of administration, the particular condition being treated and the desired outcome. It may also depend upon the stage of the condition, the age and physical condition of the subject, the nature of concurrent therapy, if any, and like factors well known to the medical practitioner. For therapeutic applications, it is that amount sufficient to achieve a medically desirable result.

With respect to a subject having a cardiac disease or disorder induced by anthracylines, an effective amount is sufficient to prevent, reduce, stabilize, or reverse an alteration associated with cardiotoxicity induced by the anthracycline. With respect to a subject having a cardiac disease or disorder induced by anthracyclines, an effective amount is an amount sufficient to stabilize, slow, or reduce a symptom associated with the cardiac condition. Generally, doses of the compounds of the present invention would be from about 0.01 mg/kg per day to about 1000 mg/kg per day. In one embodiment, 25, 50, 75, 100, 125, 150 or 200 mg/kg bodyweight of lapatinib is administered to a subject. Preferably, 25 to 100 mg/kg of lapatinib is administered. Desirably, the lapatinib is administered in an amount sufficient to achieve a peak concentration in plasma. It is expected that doses ranging from about 5 to about 2000 mg/kg will be suitable. Lower doses will result from certain forms of administration, such as intravenous administration and pharmaceutical. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of a composition of the present invention.

A variety of administration routes are available. The methods of the invention, generally speaking, may be practiced using any mode of administration that is medically acceptable, meaning any mode that produces effective levels of the active compounds without causing clinically unacceptable adverse effects. In one preferred embodiment, a composition of the invention is administered orally. Other modes of administration include rectal, topical, intraocular, buccal, intravaginal, intracisternal, intracerebroventricular, intratracheal, nasal, transdermal, within/on implants, or parenteral routes. The term "parenteral" includes subcutaneous, intrathecal, intravenous, intramuscular, intraperitoneal, or infusion. Intravenous or intramuscular routes are not particularly suitable for long-term therapy and prophylaxis. They could, however, be preferred in emergency situations. Compositions comprising a composition of the invention can be added to a physiological fluid, such as blood. Oral administration can be preferred for prophylactic treatment because of the convenience to the patient as well as the dosing schedule.

Pharmaceutical compositions of the invention can comprise one or more pH buffering compounds to maintain the pH of the formulation at a predetermined level that reflects physiological pH, such as in the range of about 5.0 to about 8.0. The pH buffering compound used in the aqueous liquid formulation can be an amino acid or mixture of amino acids, such as histidine or a mixture of amino acids such as histidine and glycine. Alternatively, the pH buffering compound is preferably an agent which maintains the pH of the formulation at a predetermined level, such as in the range of about 5.0 to about 8.0, and which does not chelate calcium ions. Illustrative examples of such pH buffering compounds include, but are not limited to, imidazole and acetate ions. The pH buffering compound may be present in any amount suitable to maintain the pH of the formulation at a predetermined level.

Pharmaceutical compositions of the invention can also contain one or more osmotic modulating agents, i.e., a compound that modulates the osmotic properties (e.g., tonicity, osmolality and/or osmotic pressure) of the formulation to a level that is acceptable to the blood stream and blood cells of recipient individuals. The osmotic modulating agent can be an agent that does not chelate calcium ions. The osmotic modulating agent can be any compound known or available to those skilled in the art that modulates the osmotic properties of the formulation. One skilled in the art may empirically determine the suitability of a given osmotic modulating agent for use in the inventive formulation. Illustrative examples of suitable types of osmotic modulating agents include, but are not limited to: salts, such as sodium chloride and sodium acetate; sugars, such as sucrose, dextrose, and mannitol; amino acids, such as glycine; and mixtures of one or more of these agents and/or types of agents. The osmotic modulating agent(s) may be present in any concentration sufficient to modulate the osmotic properties of the formulation.

Compositions comprising a compound of the present invention can contain multivalent metal ions, such as calcium ions, magnesium ions and/or manganese ions. Any multivalent metal ion that helps stabilizes the composition and that will not adversely affect recipient individuals may be used. The skilled artisan, based on these two criteria, can determine suitable metal ions empirically and suitable sources of such metal ions are known, and include inorganic and organic salts.

Pharmaceutical compositions of the invention can also be a non-aqueous liquid formulation. Any suitable non-aqueous liquid may be employed, provided that it provides stability to the active agents (s) contained therein. Preferably, the non-aqueous liquid is a hydrophilic liquid. Illustrative examples of suitable non-aqueous liquids include: glycerol; dimethyl sulfoxide (DMSO); polydimethylsiloxane (PMS); ethylene glycols, such as ethylene glycol, diethylene glycol, triethylene glycol, polyethylene glycol ("PEG") 200, PEG 300, and PEG 400; and propylene glycols, such as dipropylene glycol, tripropylene glycol, polypropylene glycol ("PPG") 425, PPG 725, PPG 1000, PPG 2000, PPG 3000 and PPG 4000.

Pharmaceutical compositions of the invention can also be a mixed aqueous/non-aqueous liquid formulation. Any suitable non-aqueous liquid formulation, such as those described above, can be employed along with any aqueous liquid formulation, such as those described above, provided that the mixed aqueous/non-aqueous liquid formulation provides stability to the compound contained therein. Preferably, the non-aqueous liquid in such a formulation is a hydrophilic liquid. Illustrative examples of suitable non-aqueous liquids include: glycerol; DMSO; PMS; ethylene glycols, such as PEG 200, PEG 300, and PEG 400; and propylene glycols, such as PPG 425, PPG 725, PPG 1000, PPG 2000, PPG 3000 and PPG 4000.

Suitable stable formulations can permit storage of the active agents in a frozen or an unfrozen liquid state. Stable liquid formulations can be stored at a temperature of at least −70° C., but can also be stored at higher temperatures of at least 0° C., or between about 0.1° C. and about 42° C., depending on the properties of the composition. It is generally known to the skilled artisan that proteins and polypeptides are sensitive to changes in pH, temperature, and a multiplicity of other factors that may affect therapeutic efficacy.

Other delivery systems can include time-release, delayed release or sustained release delivery systems. Such systems can avoid repeated administrations of compositions of the invention, increasing convenience to the subject and the physician. Many types of release delivery systems are available and known to those of ordinary skill in the art. They include polymer base systems such as polylactides (U.S. Pat. No. 3,773,919; European Patent No. 58,481), poly(lactide-glycolide), copolyoxalates, polycaprolactones, polyesteramides, polyorthoesters, polyhydroxybutyric acids, such as poly-D-(−)-3-hydroxybutyric acid (European Patent No. 133,988), copolymers of L-glutamic acid and gamma-ethyl-L-glutamate (Sidman, K. R. et al., Biopolymers 22: 547-556), poly(2-hydroxyethyl methacrylate) or ethylene vinyl acetate (Langer, R. et al., J. Biomed. Mater. Res. 15:267-277; Langer, R. Chem. Tech. 12:98-105), and polyanhydrides.

Other examples of sustained-release compositions include semi-permeable polymer matrices in the form of shaped articles, e.g., films, or microcapsules. Delivery systems also include non-polymer systems that are: lipids including sterols such as cholesterol, cholesterol esters and fatty acids or neutral fats such as mono- di- and tri-glycerides; hydrogel release systems such as biologically-derived bioresorbable hydrogel (i.e., chitin hydrogels or chitosan hydrogels); sylastic systems; peptide based systems; wax coatings; compressed tablets using conventional binders and excipients; partially fused implants; and the like. Specific examples include, but are not limited to: (a) erosional systems in which the agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480.

Another type of delivery system that can be used with the methods and compositions of the invention is a colloidal dispersion system. Colloidal dispersion systems include lipid-based systems including oil-in-water emulsions, micelles, mixed micelles, and liposomes. Liposomes are artificial membrane vessels, which are useful as a delivery vector in vivo or in vitro. Large unilamellar vessels (LUV), which range in size from 0.2-4.0 µm, can encapsulate large macromolecules within the aqueous interior and be delivered to cells in a biologically active form (Fraley, R., and Papahadjopoulos, D., Trends Biochem. Sci. 6: 77-80).

Liposomes can be targeted to a particular tissue by coupling the liposome to a specific ligand such as a monoclonal antibody, sugar, glycolipid, or protein. Liposomes are commercially available from Gibco BRL, for example, as LIPOFECTIN™ and LIPOFECTACE™, which are formed of cationic lipids such as N-[1-(2,3 dioleyloxy)-propyl]-N,N,N-trimethylammonium chloride (DOTMA) and dimethyl dioctadecylammonium bromide (DDAB). Methods for making liposomes are well known in the art and have been described in many publications, for example, in DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Liposomes also have been reviewed by Gregoriadis, G., Trends Biotechnol., 3: 235-241).

Another type of vehicle is a biocompatible microparticle or implant that is suitable for implantation into a mammalian recipient. Exemplary bioerodible implants that are useful in accordance with this method are described in PCT International application no. PCT/US/03307 (Publication No. WO 95/24929, entitled "Polymeric Gene Delivery System"). PCT/US/0307 describes biocompatible, preferably biodegradable polymeric matrices for containing an exogenous gene under the control of an appropriate promoter. The polymeric matrices can be used to achieve sustained release of the exogenous gene or gene product in the subject.

The polymeric matrix preferably is in the form of a microparticle such as a microsphere (wherein an agent is dispersed throughout a solid polymeric matrix) or a microcapsule (wherein an agent is stored in the core of a polymeric shell). Microcapsules of the foregoing polymers containing drugs are described in, for example, U.S. Pat. No. 5,075,109. Other forms of the polymeric matrix for containing an agent include films, coatings, gels, implants, and stents. The size and composition of the polymeric matrix device is selected to result in favorable release kinetics in the tissue into which the matrix is introduced. The size of the polymeric matrix further is selected according to the method of delivery that is to be used. Preferably, when an aerosol route is used the polymeric matrix and composition are encompassed in a surfactant vehicle. The polymeric matrix composition can be selected to have both favorable degradation rates and also to be formed of a material, which is a bioadhesive, to further increase the effectiveness of transfer. The matrix composition also can be selected not to degrade, but rather to release by diffusion over an extended period of time. The delivery system can also be a biocompatible microsphere that is suitable for local, site-specific delivery. Such microspheres are disclosed in Chickering, D. E., et al., Biotechnol. Bioeng., 52: 96-101; Mathiowitz, E., et al., Nature 386: 410-414.

Both non-biodegradable and biodegradable polymeric matrices can be used to deliver the compositions of the invention to the subject. Such polymers may be natural or synthetic polymers. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene, polyvinylpyrrolidone, and polymers of lactic acid and glycolic acid, polyanhydrides, poly(ortho)esters, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Methods of Treatment

In one embodiment, the present invention provides a method of enhancing survival or cardiac function in a subject treated with doxorubicin comprising the step of administering to the subject an effective amount of lapatinib and/or rapamycin, preferably as part of a composition additionally comprising a pharmaceutically acceptable carrier. Preferably this method is employed to treat a subject suffering from or susceptible to a cardiac condition induced by anthracycline treatment. Other embodiments include any of the methods herein wherein the subject is identified as in need of the indicated treatment.

Another aspect of the invention is the use of lapatinib and/or rapamycin in the manufacture of a medicament for enhancing cardiac function in a subject treated with anthracylines. Preferably, the medicament is used for treatment or prevention in a subject of a disease, disorder or symptom set forth above.

Kits

The invention provides kits for the treatment or prevention of a cardiac condition associated with anthracycline treatment. In one embodiment, the kit includes a pharmaceutical pack comprising an effective amount of lapatanib and/or rapamycin. Preferably, the compositions are present in unit dosage form. In some embodiments, the kit comprises a sterile container which contains a therapeutic or prophylactic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

If desired compositions of the invention or combinations thereof are provided together with instructions for administering them to a subject having or at risk of developing a cardiac condition associated anthracycline treatment. The instructions will generally include information about the use of lapatinib and/or rapamycin for the treatment or prevention of a cardiac condition associated with anthracycline treatment. In other embodiments, the instructions include at least one of the following: description of lapatinib; dosage schedule and administration for treatment of a cardiac condition or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Lapatinib Treatment Increased the Survival Rate of Doxorubicin-Treated Mice

Female FVB/n mice between 10 and 12 weeks old were treated with doxorubicin (2 mg/kg) by intraperitoneal injection (i.p.) twice a week for 7 weeks. This resulted in an accumulated dose of 20 mg/kg. After completion of the doxorubicin treatment cycle, the mice were subsequently treated with various doses of lapatinib (25, 50, and 100 mg/kg, given by oral gavage, daily) or with vehicle control. As shown in FIG. 1, lapatinib improved survival of doxorubicin treated mice. Sixty-four days after the initiation of doxorubicin treatment, the survival of doxorubicin treated mice was 68%, doxorubicin+lapatinib treated mice (25 mg/kg) was 100%, doxorubicin+lapatinib treated mice (50 mg/kg) was 83%, and doxorubicin+lapatinib treated mice (100 mg/kg) was 71%. Seventy days after the initiation of doxorubicin treatment, the survival of the doxorubicin treated mice was 34% while that of the doxorubicin+lapatinib (100 mg/kg) treated mice was 55%. Thus, treatment with lapatinib promoted the survival of doxorubicin treated mice.

Example 2

Lapatinib Treatment Improved Cardiac Function in Doxorubicin-Treated Mice

Figure 2A:
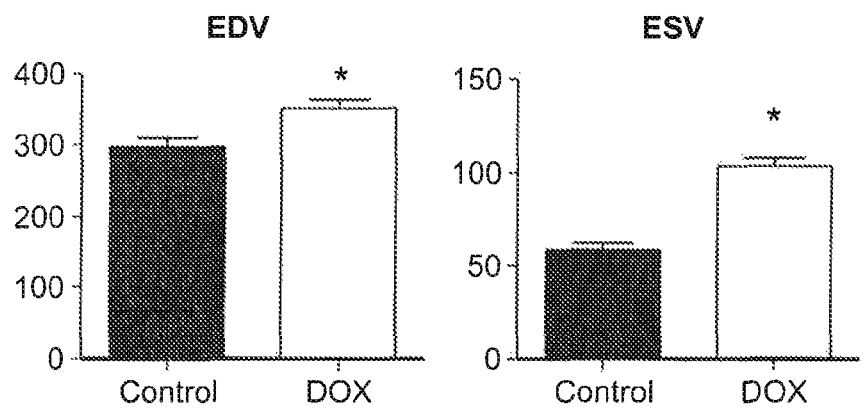
FIG. 2A and FIG. 2B are bar graphs showing the results of echocardiography in mice treated with doxorubicin for seven weeks compared to untreated controls.
Figure 2B:
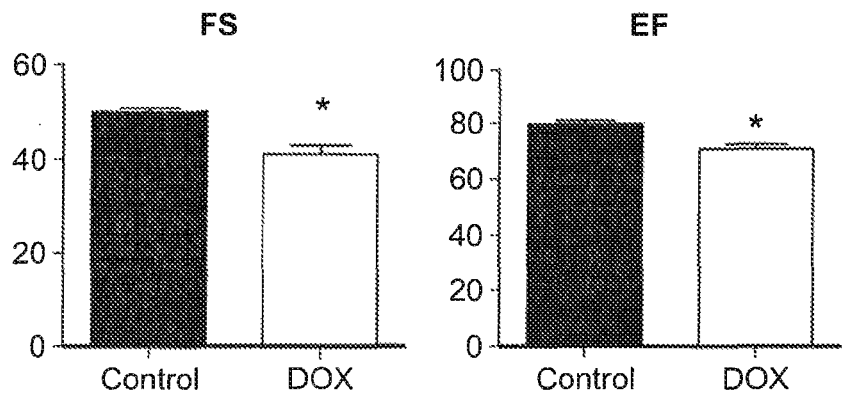
Figure 3A:
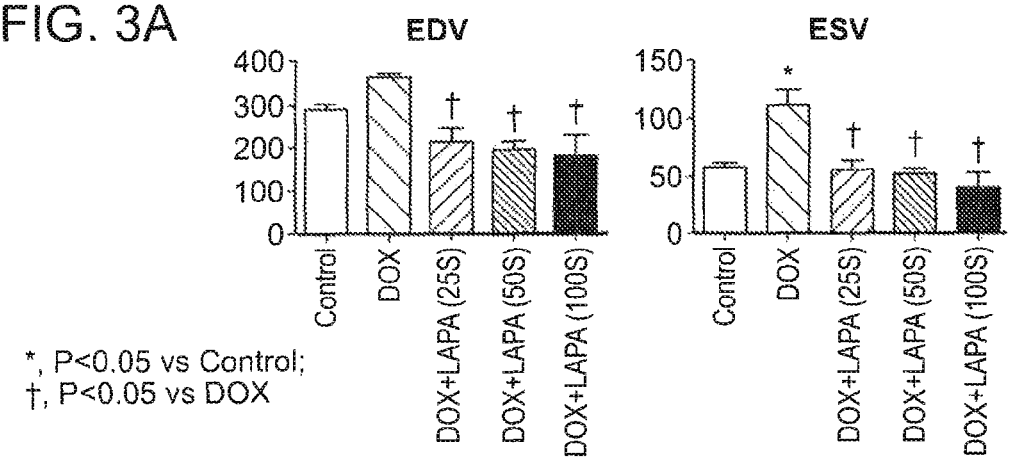
FIG. 3A and FIG. 3B are bar graphs showing the results of echocardiography in mice treated with doxorubicin followed by treatment with various doses of lapatinib.
Figure 3B:
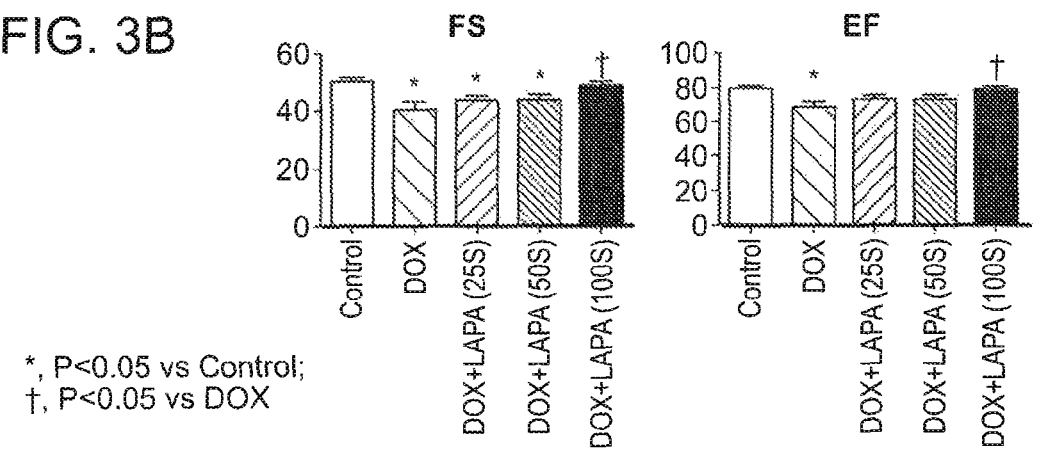
Figure 4:
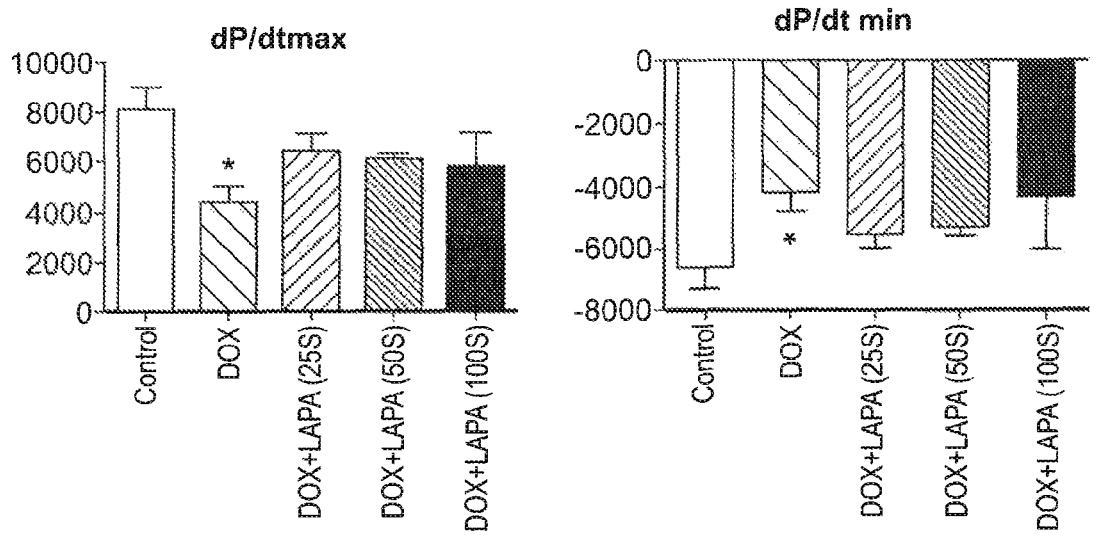
FIG. 4 is a set of graphs showing the results of hemodynamic measurements in mice treated with doxorubicin followed by treatment with various doses of lapatinib.

Cardiac function of the doxorubicin and doxorubicin+lapatinib treated mice was evaluated by echocardiography. As shown in FIG. 2A and FIG. 2B, seven weeks after the completion of the doxorubicin treatment, the end-systolic volume (ESV) was increased in doxorubicin treated mice, which was associated with decreased ejection fraction (EF %), indicating that the doxorubicin treated mice developed dilated cardiomyopathy and heart failure. Three weeks after the initiation of lapatinib treatment (nine weeks after the initiation of the doxorubicin treatment), cardiac function as measured by echocardiography and hemodynamic measurements was significantly decreased in doxorubicin treated mice compared to control mice, but was improved in doxorubicin+lapatinib treated versus doxorubicin treated mice. As shown in FIG. 3A and FIG. 3B, ESV was significantly increased in doxorubicin treated versus control mice, which was associated with decreased EF %; doxorubicin+lapatinib treatment reversed these effects of doxorubicin. As shown in FIG. 4, dP/dtmax and dP/dtmin were significantly decreased in doxorubicin treated vs. control mice, while these indices were not different between doxorubicin+lapatinib treated and control mice. These results indicate that lapatinib treatment improved cardiac function in doxorubicin-treated mice that had pre-existing heart failure. These results indicate that lapatinib is useful for the treatment of doxorubicin-induced heart failure.

Example 3

Figure 5:
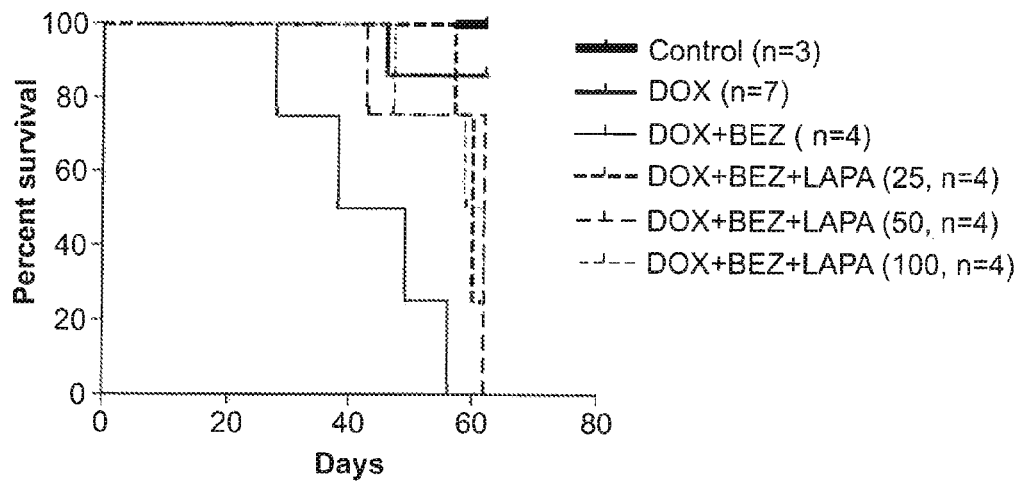
FIG. 5 is a graph showing the survival curve of mice treated with doxorubicin, the PI3K-mTOR inhibitor BEZ235 and various doses of lapatinib.
Figure 6A:
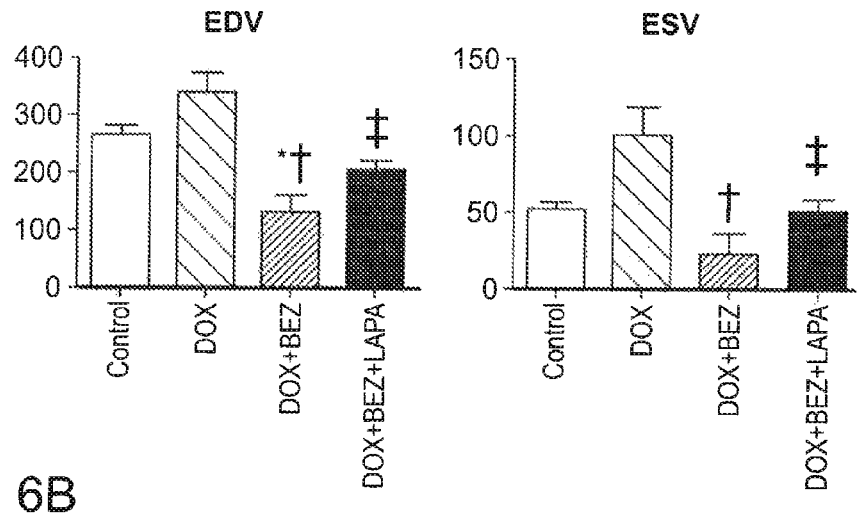
FIG. 6A, FIG. 6B, FIG. 6C, and FIG. 6D are bar graphs showing the results of echocardiography in mice treated with doxorubicin, BEZ235 and various doses of lapatinib.
Figure 6B:
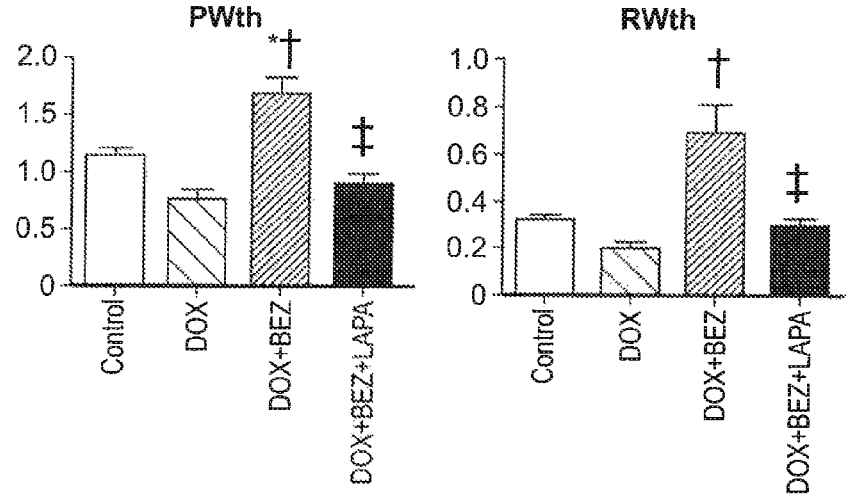
Figure 6C:
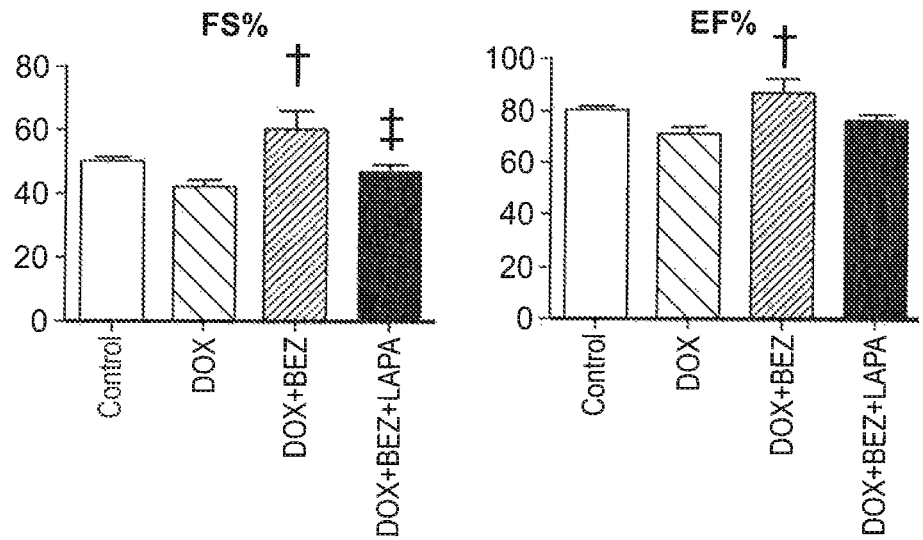
Figure 6D:
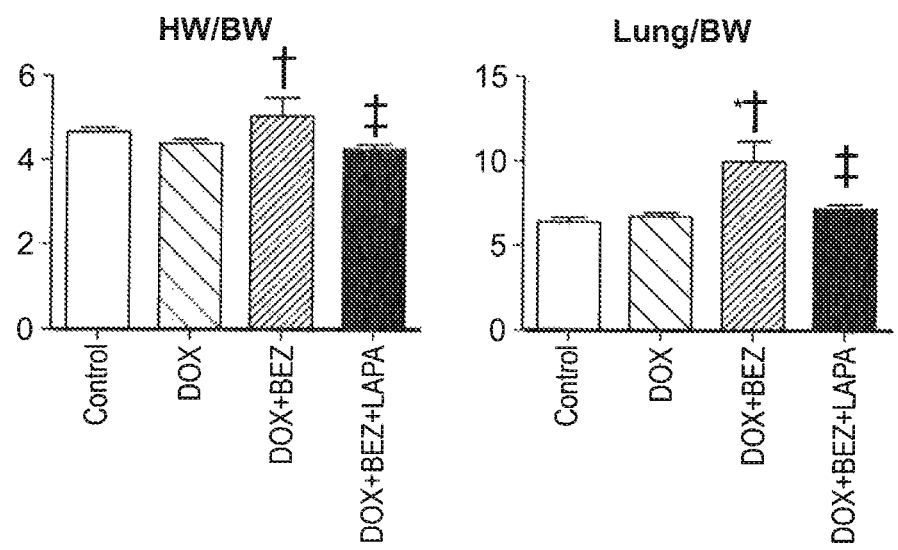

Lapatinib Treatment Improved Survival in Mice Co-Treated with Doxorubicin and PI3K-mTOR Inhibitor Combined doxorubicin and kinase inhibitor treatments are necessary for effective cancer control in certain patients. It is important to know whether this type of therapy will cause cardiotoxicity, and if so, how to reduce this cardiac risk. FVB/n female mice were treated with doxorubicin (2 mg/kg, i.p.) twice a week, PI3 kinase-mTOR inhibitor BEZ235 (35-50 mg/kg, oral, daily) and lapatinib (25, 50 or 100 mg/kg, oral, daily). Cardiac function was monitored by echocardiography. Doxorubicin+BEZ235 treatment reduced survival, while lapatinib prolonged the lifespan of doxorubicin+BEZ235 treated mice. As shown in FIG. 5, survival was significantly reduced in doxorubicin+BEZ235 treated vs. doxorubicin treated mice. Survival was significantly improved in doxorubicin+BEZ235+lapatinib versus doxorubicin+BEZ235 treated mice.

Example 4

Lapatinib Treatment Cardiac Function in Mice Co-Treated with Doxorubicin and PI3K-mTOR Inhibitor Doxorubicin+BEZ235 treatment induced cardiac hypertrophy in mice. However, lapatinib treatment reversed this effect. As shown in FIG. 6A, FIG. 6B, FIG. 6C, and FIG. 6D, co-treatment with doxorubicin+BEZ235 reduced end-diastolic volume (EDV) and end-systolic volume (ESV), which were associated with increased relative wall thickness (RWth), EF %, heart weight to body weight ratio (HW/BW) and lung to body weight ratio. These results indicate that doxorubicin+BEZ235 treated mice developed cardiac hypertrophy and diastolic heart failure. Lapatinib co-treatment reversed these effects. These results indicate that lapatinib is useful for preventing doxorubicin+BEZ235 induced cardiac hypertrophy and failure.

Example 5

Rapamycin Enhanced Cardiac Function and Survival in Doxorubicin Treated Mice

Mice were treated with doxorubicin (2 mg/kg) by intraperitoneal injection twice a week for 7 weeks for an accumulation dose of 20 mg/kg. After the completion of doxorubicin treatment, mice were subsequently treated with either Lapatinib alone (100 mg/kg, oral gavage, daily) or Rapamycin alone (6 mg/kg, i.p., daily). Survival was monitored. Cardiac function was assessed by hemodynamic measurements.

Ten weeks after the initiation of doxorubicin treatment, survival was significantly improved in Lapatinib vs. Solvent treated doxorubicin injured mice (71% vs. 43%). Cardiac function as measured by cardiac output was significantly decreased in Solvent treated doxorubicin injured mice vs. non-treated control mice. No difference was observed between Lapatinib treated doxorubicin injured mice vs. non-treated control mice.

Ten weeks after the initiation of doxorubicin treatment, survival was significantly improved in Rapamycin vs. Solvent treated DOX injured mice (63% vs. 43%). Cardiac function as measured by cardiac output was significantly decreased in Solvent treated DOX injured mice vs. non-treated Control mice. This decrease in cardiac function was not observed in DOX-injured mice treated with Rapamycin.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of treating anthracycline induced cardiotoxicity comprising administering an effective amount of lapatinib and/or rapamycin to a subject in need thereof, thereby treating the anthracycline induced cardiotoxicity.

2. A method of enhancing cardiac function or increasing survival in a subject treated with an anthracycline comprising administering an effective amount of lapatinib to the subject, thereby improving cardiac function in the subject.

3. The method of claim 1, wherein the method reduces cardiac hypertrophy and adverse cardiac remodeling in the subject.

4. The method of claim 1, wherein the anthracycline is selected from the group consisting of daunorubicin, doxorubicin, epirubicin, idarubicin, valrubicin, and mitoxantrone.

5. The method of claim 1, wherein the anthracycline is doxorubicin.

6. The method of claim 1, further comprising determining the subject's cumulative lifetime dose of anthracycline and administering the effective amount of lapatinib and/or rapamycin if the cumulative lifetime dose is above a reference value.

7. The method of claim 1, wherein the effective amount of lapatinib is from 25 to 100 mg/kg administered daily.

8. The method of claim 1, wherein the effective amount of lapatinib is about 25 mg/kg administered daily.

9. The method of claim 1, wherein the subject is identified by echocardiography.

* * * * *